United States Patent [19]

Dougherty et al.

[11] 4,330,280
[45] May 18, 1982

[54] EJECTOR HOLDER FOR CAPSULE-LIKE CARTRIDGE

[75] Inventors: Emery W. Dougherty; Richard E. Welsh, both of Milford, Del.

[73] Assignee: Dentsply Research & Development Corp., Milford, Del.

[21] Appl. No.: 252,558

[22] Filed: Apr. 9, 1981

[51] Int. Cl.³ .............................................. A61C 5/04
[52] U.S. Cl. .................................. 433/90; 222/326
[58] Field of Search .............. 433/90, 89; 222/326, 222/386, 325, 327

[56] References Cited

U.S. PATENT DOCUMENTS

| | | | |
|---|---|---|---|
| 3,581,399 | 6/1971 | Dragan | 433/90 |
| 3,900,954 | 8/1975 | Dragan | 433/90 |
| 4,198,756 | 4/1980 | Dragan | 433/90 |

*Primary Examiner*—Robert Peshock
*Attorney, Agent, or Firm*—C. Hercus Just

[57] ABSTRACT

A manually operable ejector holder for a loaded capsule-like cartridge of cylindrical shape open at one end and provided with an annular flange at the open end, the other end being closed but provided with an angular discharge nipple and the holder having a cylindrical body provided with an ejecting plunger operated by a pivoted lever-type handle member. The forward end of the cylindrical body being partially cutaway in a radial direction for a limited distance longitudinally to provide a hollow seat to receive the flanged end of the cartridge and the seat having an undercut groove to receive the flange of said cartridge, and the sidewalls of the seat at the upper edges being of limited flexibility and spaced apart a slightly less distance than the diameter of the cartridge body to effect a limited snap-acting connection of the cartridge to the holder.

4 Claims, 7 Drawing Figures

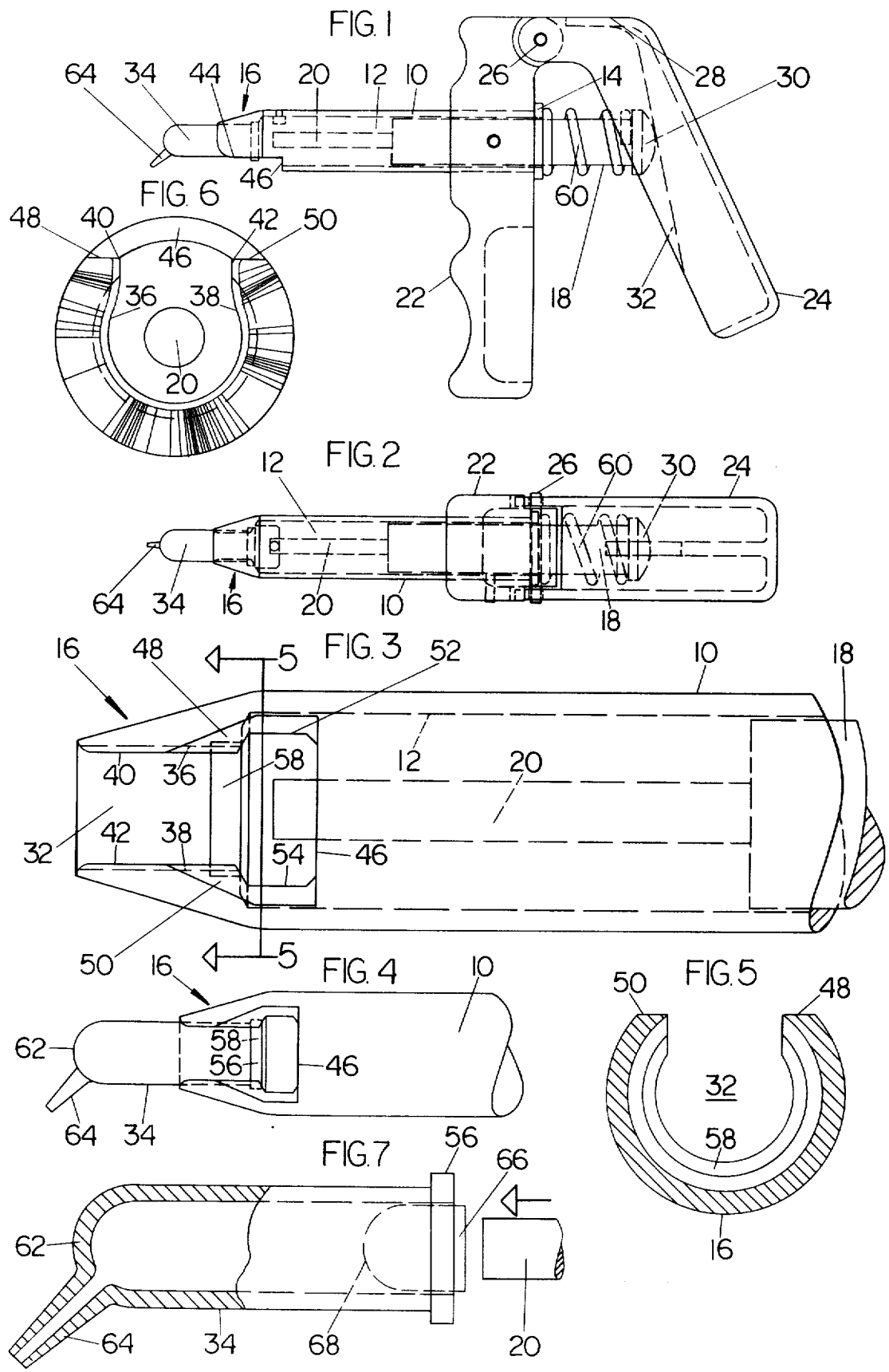

EJECTOR HOLDER FOR CAPSULE-LIKE CARTRIDGE

BACKGROUND OF THE INVENTION

In recent years it has become popular to package various types of material, especially medicinal or quasi-medicinal types in sealed cartridges, insertable in a suitable type of holder and/or ejector device, for purposes of preserving purity of the medicament and the like, insuring a patient of accurately measured quantities, as well as minimizing effort now required in introducing bulk amounts of material in a syringe and ejecting measured quantities thereof, for example. Various previous efforts in this direction are illustrated and described in various prior U.S. patents, particularly U.S. Pat. No. 3,581,399 Dragan, dated June 1, 1971, in which a typical example of loaded cartridge is illustrated in conjunction with one type of holder and discharge device. The present invention primarily comprises an improvement over this particular patented structure.

Other efforts have been made to produce similar devices, one of these comprising the subject matter of prior U.S. Pat. No. 3,900,954, also to Dragan, dated Aug. 26, 1975, and comprising a simpler version than in Dragan's U.S. Pat. No. 3,581,399.

It has been found in the operation of the Dragan devices, particularly relative to the curved discharge end of the capsule or cartridges that there have been occasions when the leading end of the ejecting plunger or the piston within the cartridge pushed through the wall adjacent the outer end of the cartridge. Particularly for purposes of obviating this difficulty and also for providing what is believed to be a simple and improved compartment at the forward end of the barrel of the holder, as well as also providing an improved cartridge not subject to the difficulties of Dragan's cartridges, which is free of difficulties similar to those described with respect to the Dragan cartridge, the present invention has been devised and details thereof are set forth hereinbelow.

The present invention also comprises a simplified improvement over co-pending application, Ser. No. 190,681 in the name of Helmut Rudler, filed Sept. 25, 1980, and entitled "Ejector Holder for Syringe-type Cartridge", the invention covered thereby being assigned to the same assignee as the invention of the instant application.

SUMMARY OF THE INVENTION

It is among the principal objects of the present invention to provide preferably a one-piece barrel having integral and relatively simple means at the forward end thereof to seat and retain an improved cartridge having an annular flange at the end opposite the discharge end, said cartridge being retained by a simple snap-acting arrangement.

It is another object of the invention to provide at the forward end of said barrel a compartment in which said aforementioned seat for the flange of the cartridge is included, said compartment being formed simply by cutting away part of the wall comprising the forward end of the barrel a limited distance inwardly and axially from the outer end of the barrel, the surface formed by the cutaway arrangement lying within a plane parallel to the axis and radially spaced from the same, the inner end portion of the cutaway arrangement being wider than the portion extending forwardly therefrom for purposes of receiving the flange of the cartridge and the seat for said flange being forwardly of the inner end of the compartment through which the flange is inserted into the compartment.

A further object of the invention is to provide in the compartment a semi-cylindrical surface from which opposite, substantially parallel sidewalls extend and the upper edges of said sidewalls extending a very limited distance toward each other and said sidewalls having limited flexibility to provide the snap-acting retaining arrangement referred to above.

Still another object of the invention is to provide an improved cartridge having a cylindrical elongated body open at one end and provided with a circular flange exteriorly thereof and the opposite end of the cartridge being hemispherical and includes an angularly extending discharge nipple having a relatively small diameter elongated opening, said cartridge readily being rotatable about its axis when mounted within the barrel in order to direct the discharge at any angle desired by the operator, the cartridge being of uniform diameter exteriorly, as well as interiorly, and also including a piston having sidewalls complementary to the inner walls of the body and inserted into the open end thereof to form a closure and also being formed on the inner end of the piston in hemispherical configuration and complementary to the interior surface of the closed end of the body of the cartridge, thereby eliminating any possibility of the piston rupturing the closed end of the cartridge and also insuring maximum delivery of material from the cartridge when the piston is fully inserted therein.

Details of the foregoing objects and of the invention, as well as other objects thereof, are set forth in the following specification and illustrated in the accompanying drawing comprising a part thereof.

BRIEF DESCRIPTION OF THE DRAWING

FIG. 1 is a side elevation of an ejector holder supporting a capsule-like cartridge in accordance with the principles of the present invention.

FIG. 2 is a top plan view of the holder and cartridge shown in FIG. 1.

FIG. 3 is a fragmentary enlarged bottom plan view of the forward end of the barrel of the ejector holder shown in FIGS. 1 and 2.

FIG. 4 is a fragmentary bottom plan view of the ejector holder similar to FIG. 3, but on a smaller scale, and illustrating a cartridge supported in the forward end of the barrel.

FIG. 5 is a vertical sectional view of the forward end portion of the barrel of the ejector holder shown in FIG. 3, as seen on the line 5—5 thereof.

FIG. 6 is a front end view of the forward end of the barrel shown in FIGS. 1-4.

FIG. 7 is a side elevation, partly broken away, of a cartridge similar to that shown in FIGS. 1, 2 and 4, but on a larger scale, and illustrating a piston inserted in the open end of the cartridge and also showing fragmentarily a portion of a plunger rod of the ejector holder adapted to engage said piston.

DETAILED DESCRIPTION OF THE PREFERRED EMBODIMENT

Referring to FIG. 1, there is shown therein an ejector holder embodying the principles of the present invention and comprising a barrel 10 having an interior bore 12 extending from the rearward end 14 of the barrel toward the forward end 16 thereof for purposes of receiving a plunger 18 of the same diameter as that of the interior bore 12 for the major portion of the length of the plunger, the forward end of the plunger having a smaller diameter extension 20.

The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26. The upper end 28 of operating lever 24 is offset laterally to facilitate operation of the lever 24 with respect to the outer end of plunger 18 which terminates in a button 30 engageable by the inner surface 32 of operating lever 24.

From FIGS. 1-4, it will be seen that the forward end 16 of the barrel 10 is tapered and is provided with a longitudinally extending opening comprising compartment 32 which extends rearwardly from the terminal end of the forward end 16 toward the interior bore 12. The lower surface of compartment 32, as viewed in FIG. 3, is semi-cylindrical and is complementary to the elongated body of cartridge 34 so as to receive and seat the same, as shown in FIGS. 1, 2 and 4. However, the sidewalls 36 and 38 of compartment 32 extend upwardly from the semi-cylindrical bottom surface shown in FIG. 3 and are parallel to each other for a limited distance and the upper edges 40 and 42 extend toward each other a limited distance. Said uppermost portions of sidewalls 36 and 38 also have limited flexibility, whereby the distance between the upper edges 40 and 42 of said sidewalls is slightly less than the diameter of the cartridge 34, whereby there is a snap-acting retaining function provided by said sidewalls and the upper edges 40 and 42 with respect to the cartridge 34 when the latter is inserted in the compartment 32.

The forward end 16 of the barrel 10 also has a cutaway portion 44 extending longitudinally rearward to form a shoulder 46, which determines the inner end of the cutaway portion. Due to the fact that the forward end 16 is tapered and the barrel 10 otherwise is circular, said cutaway arrangement provides flat surfaces 48 and 50. Also, as best shown in FIG. 3, the sidewalls of the compartment 32, at the inner ends thereof, have lateral recesses 52 and 54 which are spaced apart a greater distance than the diameter of the annular exterior flange 56 in order to permit the insertion of the flange into compartment 32 which, following radial insertion movement thereof into the compartment, the cartridge may be moved axially forward for disposition of the flange 56 in an undercut seat 58, which is clearly shown in FIGS. 3-5. Said seat, in conjunction with the portion of the compartment 32 extending forwardly therefrom, provides a firm means for supporting a cartridge 34, which is retained seated in said compartment, especially by means of the snap-fitting arrangement provided by the upper edges 40 and 42 of the sidewalls 36 and 38, as described hereinabove.

Without restriction thereto, the preferred material from which the barrel 10, handle member 22 and operating lever 24 are formed, is a suitable rigid plastic material in order that these elements may be formed readily and accurately by molding from raw plastic material; obviously, the coiled spring 60 is formed from spring wire for purposes of retracting the plunger 18 when the operating lever 24 is released, following an ejection of material from the cartridge 34. Similarly, the cartridge 34 also is formed by molding from appropriate, preferably rigid synthetic resin or plastic material by means of a suitable mold. The intermediate body portion of the capsule 34 is of uniform interior and exterior diameter and extends from the flange 56 adjacent the open end of the cartridge to the opposite closed end 62. The body portion is cylindrical, whereas the closed end 62 is hemispherical but is provided with an angularly extending discharge nipple 64, the opening of which is preferably a very fine dimension of small diameter. To effect ejection of material from the cartridge 34, such as dental filling material, cement, or other viscous dental material and the like, for example, the cartridge 34 includes a piston 66, which is closely complementary in diameter to the interior of the cartridge 34, and the inner end 68 thereof also is hemispherical and complementary to the interior of the closed end 62 of the cartridge. The outer end of the piston may be flat for engagement, for example, with the extension 20, shown fragmentarily in FIG. 7, when the plunger 18 is moved forwardly by actuation of the operating lever 24.

Removal of the capsule 34 from the compartment 32 is accomplished readily by snapping the cartridge outwardly beyond the somewhat flexible upper edges 40 and 42 of the compartment after the contents within the cartridge have been discharged or exhausted, as required.

From the foregoing, it will be seen that the ejector holder and the particular type of cartridge to be used therewith are of very simple, but highly effective design, to permit sure and quick mounting of the cartridge within the compartment in the forward end of the barrel of the holder and, with equal facility, removal of the cartridge therefrom is readily achieved. Assembly of all of the components, particularly when manufactured by molding of suitable plastic or synthetic resin assures accurate dimensions and the design of all the components is such that they are readily capable of being formed by molding from plastic material.

Not only is the cartridge capable of serving as a receptacle for material to be discharged when filled, for example, from a storage amount, but, even more importantly, the cartridge can be filled at a factory with predetermined quantities of material and sealed therein by application of the piston 66, which, under the circumstance, serves as a closure for the cartridge. Further, during filling, air in the cartridge in advance of the material can be discharged through the nipple 64 until filled and then the open end of the nipple may suitably and inexpensively be closed by suitable seal means, such as a small piece of sheet material having pressure-sensitive cement on one side and fold said piece across the nipple in any suitable manner.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A manually operable ejector holder and a loaded capsule-like cartridge in which said cartridge has an annular collar on one end and a discharge tip on the other, and said holder comprising in combination, an elongated barrel, a plunger reciprocable therein and one end projecting beyond said barrel, manually operable lever means on one end of said barrel operable to reciprocate said plunger relative to the other end of said barrel, and said other end of the barrel being cutaway longitudinally a limited distance to provide a compartment having sidewalls extending a limited distance beyond the axis of said barrel, an undercut groove formed in said compartment within said sidewalls to receive the annular collar on said cartridge to prevent relative axial movement between said cartridge and compartment, and the outer longitudinally-extending portions of the sidewalls of said compartment having limited flexibility and extending toward each other a slightly lesser distance than the diameter of said cartridge to effect a snap-acting retaining means for said cartridge when inserted into said compartment.

2. The ejector holder according to claim 1 in which the sidewalls of said compartment at the inner end thereof are recessed laterally a greater distance than the diameter of the annular flange on said cartridge to permit said flange to be inserted into said compartment incident to being positioned into said undercut groove, and said undercut groove at the upper ends thereof having opposite wall portions of said compartment extending toward each other a limited distance less than the diameter of said annular cartridge flange to provide a seat for said flange forward of the portion of said laterally recessed portion of said sidewalls of said compartment from which said flange cannot be removed laterally.

3. The ejector holder according to claim 1 in which the sidewalls of said compartment forwardly of said undercut groove extend outwardly in a radial direction from a semi-cylindrical innermost surface of uniform diameter and the distance between said sidewalls being uniform throughout the length thereof forwardly of said undercut groove, and the body of said cartridge having a uniform diameter except for said flange at one end and the opposite end having a discharge nipple extending therefrom, the flange end of said cartridge being open for filling purposes and to receive a piston or plunger.

4. The ejector holder according to claim 3 in which the inner end of the interior of said cartridge is hemispherical, and a piston for said cartridge having cylindrical sidewalls and the inner end being of a hemispherical shape complementary to the inner end of the interior of said cartridge, the outer end of said piston being engageable by the outer end of said plunger.

* * * * *

REEXAMINATION CERTIFICATE (414th)

United States Patent [19]

Dougherty et al.

[11] B1 4,330,280

[45] Certificate Issued  Nov. 5, 1985

[54] EJECTOR HOLDER FOR CAPSULE-LIKE CARTRIDGE

[75] Inventors: Emery W. Dougherty; Richard E. Welsh, both of Milford, Del.

[73] Assignee: Dentsply Research & Development Corp., Milford, Del.

Reexamination Request:
No. 90/000,669, Nov. 13, 1984

Reexamination Certificate for:
Patent No.: 4,330,280
Issued: May 18, 1982
Appl. No.: 252,558
Filed: Apr. 9, 1981

[51] Int. Cl.[4] .............................................. A61C 5/04
[52] U.S. Cl. ..................................... 433/90; 222/326

[56] References Cited

U.S. PATENT DOCUMENTS

| | | | |
|---|---|---|---|
| D. 252,246 | 7/1979 | Christian | D6/246 |
| 2,505,028 | 4/1950 | Boeger | 128/215 |
| 2,803,050 | 8/1957 | Fernberg | 24/259 |
| 2,847,009 | 8/1958 | Blease | 128/222 |
| 3,076,455 | 2/1963 | McConnaughey | 128/218 |
| 3,164,303 | 1/1965 | Trautmann | 222/190 |
| 3,220,412 | 11/1965 | McConnaughey | 128/218 |
| 3,313,009 | 4/1967 | Beckerer | 24/257 |
| 3,318,224 | 5/1967 | Bohanon | 98/33 |
| 3,534,735 | 10/1970 | Sly | 128/220 |
| 3,581,399 | 6/1971 | Dragan | 433/90 |
| 3,880,106 | 4/1975 | Farmer | 115/18 E |
| 3,900,954 | 5/1975 | Dragan | 433/90 |
| 4,198,756 | 4/1980 | Dragan | 433/90 |

FOREIGN PATENT DOCUMENTS

MU5701465  7/1979  Brazil .

OTHER PUBLICATIONS

S. S. White Composite Syringe, 2 pp., Printed Prior to 11/5/79.

*Primary Examiner*—Robert Peshock

[57] ABSTRACT

A manually operable ejector holder for a loaded capsule-like cartridge of cylindrical shape open at one end and provided with an annular flange at the open end, the other end being closed but provided with an angular discharge nipple and the holder having a cylindrical body provided with an ejecting plunger operated by a pivoted lever-type handle member. The forward end of the cylindrical body being partially cutaway in a radial direction for a limited distance longitudinally to provide a hollow seat to receive the flanged end of the cartridge and the seat having an undercut groove to receive the flange of said cartridge, and the sidewalls of the seat at the upper edges being of limited flexibility and spaced apart a slightly less distance than the diameter of the cartridge body to effect a limited snap-acting connection of the cartridge to the holder.

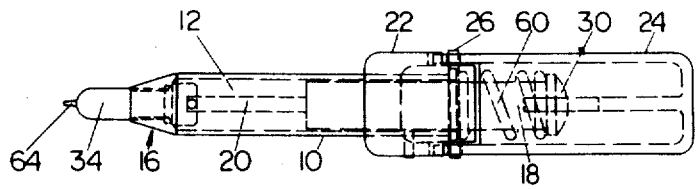

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-4 is confirmed.

New claim 5 is added and determined to be patentable.

*5. The ejector holder according to claim 1, wherein said outer longitudinally extending portions of said sidewalls extend longitudinally a distance of substantially one half the length of said cartridge.*

REEXAMINATION CERTIFICATE (1163rd)
United States Patent [19]
Dougherty et al.

[11] B2 4,330,280
[45] Certificate Issued  Dec. 5, 1989

[54] EJECTOR HOLDER FOR CAPSULE-LIKE CARTRIDGE

[75] Inventors: Emery W. Dougherty; Richard E. Welsh, both of Milford, Del.

[73] Assignee: Dentsply Research Development Corp., Milford, Del.

Reexamination Request:
No. 90/000,880, Oct. 10, 1985

Reexamination Certificate for:
Patent No.: 4,330,280
Issued: May 18, 1982
Appl. No.: 252,558
Filed: Apr. 9, 1981

Reexamination Certificate B1 4,330,280 issued Nov. 5, 1985.

[51] Int. Cl.$^4$ .................................................. A61C 5/04
[52] U.S. Cl. .................................... 433/90; 222/326
[58] Field of Search ................. 433/90, 89; 222/326, 222/386, 325, 327

[56] References Cited

U.S. PATENT DOCUMENTS

| | | | |
|---|---|---|---|
| D. 252,246 | 7/1979 | Christian | D6/246 |
| 2,505,028 | 4/1950 | Boeger | 128/215 |
| 2,803,050 | 8/1957 | Fernberg | 24/259 |
| 2,847,009 | 8/1958 | Blease | 128/222 |
| 3,076,455 | 2/1963 | McConnaughey | 128/218 |
| 3,164,303 | 1/1965 | Trautmann | 222/190 |
| 3,220,412 | 11/1965 | McConnaughey | 128/218 |
| 3,313,009 | 4/1967 | Beckerer | 24/257 |
| 3,318,224 | 5/1967 | Bohanon | 98/33 |
| 3,534,735 | 10/1970 | Sly | 128/220 |
| 3,575,318 | 4/1971 | Lemelson | 222/79 |
| 3,581,399 | 6/1971 | Dragan | 433/90 |
| 3,880,106 | 4/1975 | Farmer | 115/18 E |
| 3,900,954 | 5/1975 | Dragan | 433/90 |
| 4,198,756 | 4/1980 | Dragan | 433/90 |
| 4,384,853 | 5/1983 | Welsh | 433/90 |

FOREIGN PATENT DOCUMENTS

MU-5701465  7/1979  Brazil

OTHER PUBLICATIONS

S. S. White Composite Syringe, 2 pages, printed prior to 11/5/79.
Dental Products Report, Cleve-Dent Ad, 1 page, Sep. 1979.
Dental Management (Hygienic Ad) Sep. 1985, cited to evidence obviousness.
Dental Products Report-vivadent Ad, Sep. 1985, cited to evidence obviousness only.

*Primary Examiner*—John J. Wilson

[57] ABSTRACT

A manually operable ejector holder for a loaded capsule-like cartridge of cylindrical shape open at one end and provided with an annular flange at the open end, the other end being closed but provided with an angular discharge nipple and the holder having a cylindrical body provided with an ejecting plunger operated by a pivoted lever-type handle member. The forward end of the cylindrical body being partially cutaway in a radial direction for a limited distance longitudinally to provide a hollow seat to receive the flanged end of the cartridge and the seat having an undercut groove to receive the flange of said cartridge, and the sidewalls of the seat at the upper edges being of limited flexibility and spaced apart a slightly less distance than the diameter of the cartridge body to effect a limited snap-acting connection of the cartridge to the holder.

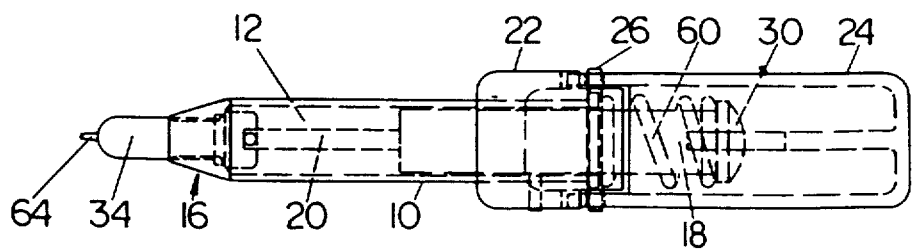

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claim 5 is cancelled.

Claims 2, 3 and 4, dependent on an amended claim, are determined to be patentable.

New claims 6, 7, 8, 9, 10, 11 and 12 are added and determined to be patentable.

1. A manually operable ejector holder and a loaded capsule-like cartridge in which said cartridge has an annular collar on one end [and], a discharge tip on the other, [and] *end, and an intermediate body portion in between,* said holder comprising in combination, an elongated barrel *having an interior bore,* a plunger reciprocable therein and one end projecting beyond said barrel, manually operable lever means on one end of said barrel operable to reciprocate said plunger relative to the other end of said barrel, and said other end of the barrel being cutaway longitudinally a limited distance to provide a compartment having side walls extending a limited distance beyond the axis of said barrel, an undercut groove formed *forward of said interior bore and rearwardly* in said compartment within said sidewalls to receive the annular collar on said cartridge to prevent relative axial movement between said cartridge and compartment, and the outer longitudinally-extending portions of the sidewalls of said compartment having limited flexibility and extending toward each other a slightly lesser distance than the diameter of said cartridge *intermediate body portion* to effect a snap-acting retaining means for said cartridge when inserted into said compartment, *said retaining means extending longitudinally a distance forward of said undercut groove substantially greater than the longitudinal length of said annular collar to hold a substantial portion of said cartridge intermediate body portion.*

*6. The ejector holder according to claim 1, having a rear portion rearward of said undercut groove to permit said flange to be inserted into said rear portion incident to being positioned into said undercut groove, said rear portion having an inner surface defined by said interior bore and having a greater distance than said undercut groove.*

*7. The ejector holder according to claim 1, wherein said compartment sidewalls forward of said undercut groove provide a forward inner surface of a diameter smaller than the diameter of said groove to accomodate said intermediate body portion.*

*8. The ejector holder according to claim 1, comprising a shoulder means at the rear end of said compartment for limiting axial movement of the cartridge in the rearward direction.*

*9. The ejector holder according to claim 6, wherein said rear portion permits placing said flange loosely in said compartment while at the same time snap-fitting said intermediate body portion into said retaining means.*

*10. The ejector holder according to claim 1, wherein said other end of the barrel is tapered laterally inward towards its forward end.*

*11. The ejector holder according to claim 1, wherein said outer sidewall portions terminate in flat surfaces.*

*12. The ejector holder according to claim 1, wherein said interior bore has a first diameter, and said undercut groove has a second diameter smaller than said first diameter.*

* * * * *